United States Patent [19]
Coleman

[11] Patent Number: 5,106,477
[45] Date of Patent: Apr. 21, 1992

[54] ELECTROPHORESIS BUFFER CIRCULATION APPARATUS

[75] Inventor: Howard C. Coleman, Seattle, Wash.

[73] Assignee: Genelex Corporation, Seattle, Wash.

[21] Appl. No.: 610,374

[22] Filed: Nov. 6, 1990

[51] Int. Cl.[5] .......................... B01D 61.42; B01D 57/02
[52] U.S. Cl. ............................... 204/299 R; 204/180.1
[58] Field of Search ....................... 204/299 R, 180.1

[56] References Cited

U.S. PATENT DOCUMENTS

| 3,104,221 | 9/1963 | Hill | 204/237 |
| 4,588,491 | 5/1986 | Kreisher | 204/299 R |
| 4,702,814 | 10/1987 | Audeh | 204/299 R |

Primary Examiner—John Niebling
Assistant Examiner—Caroline Koestner
Attorney, Agent, or Firm—Larry A. Jackson; John M. Johnson

[57] ABSTRACT

A fluid circulation apparatus for an electrophoresis device is disclosed. The fluid circulation device has an electrode gas retaining means communicating with the two reservoirs of the electrophoresis device. The electrode gas retaining means is disposed to trap electrode produced gas at a level below the fluid level in the remainder of the electrophoresis device so that fluid in the electrode gas retaining means has a pressure head greater than the pressure at the fluid level in the remainder of the electrophoresis device. The resulting fluid pressure differential causes the fluid flow between the two reservoirs of the electrophoresis device through the electrode gas retaining means.

14 Claims, 3 Drawing Sheets

ELECTROPHORESIS BUFFER CIRCULATION APPARATUS

BACKGROUND OF THE INVENTION

The present invention generally pertains to the field of electrophoresis, and specifically to an apparatus providing improved circulation of the liquid buffer solutions used in electrophoresis.

Electrophoresis devices are typically used for the separation of charged biological molecules, such as proteins and nucleic acids, by differential migration of the molecular constituents through a semi-solid matrix. The migration is caused by an electrical field induced between two electrodes connected to an external DC power supply. The rates of migration of individual macromolecules is determined by their mass and net electrical charge.

The observation that electrically charged biopolymers will migrate in response to an electrical field has led to the development of various electrophoresis techniques. In gel electrophoresis, matrices such as agarose, polyacrlyamide or starch, when placed in a liquid buffer solution, are used as a medium through which mixtures of macromolecules will migrate. The sample mixture is applied to one end of the matrix plate and current is applied across the matrix. The molecules in the sample migrate to discrete zones, or bands, based on their mass and charge.

Following electrophoresis, a wide variety of both direct and indirect techniques are used to visualize the macromolecules either within the electrophoresis matrix or following transfer to a solid support. Both analytical and preparative and qualitative and quantitative methods are known and used. Many of these methods are described in *ELECTROPHORESIS Theory, Techniques, and Biochemical and Clinical Applications*, 2nd edition, A. T. Andrews, Oxford University Press, 1986; *Current Protocols in Molecular Biology*, ed. Ausubel, F. M., et al, Wiley Interscience, 1990; and *GEL ELECTROPHORESIS OF NUCLEIC ACIDS: A Practical Approach*, ed. Rickwood, D. and Hames, B. D., IRL Press, Oxford, England, 1990.

Electrophoresis, and specifically gel electrophoresis, is widely used in clinical and forensic laboratories to separate isoproteins obtained from blood and other body fluids in order to diagnose specific disease states, or to identify the source of an evidence sample. It is also used to separate deoxyribonucleic acid (DNA) molecules for the purposes of medical genetics and individual identification. In research laboratories, electrophoresis forms the backbone technique of many life science fields, such as molecular biology and genetics and protein biochemistry.

In gel electrophoresis of macromolecules such as deoxyribonucleic acid (DNA) and ribonucleic acid (RNA), circulation of the liquid buffer solution is necessary for molecular migration to occur. Circulating the buffer overcomes imbalances in chemical and thermal conditions that develop during the course of an electrophoretic separation and that lead to distortions of the migration pattern in the gel. These distortions occur because electrophoretic separation of nucleic acids may take as many as twelve to thirty hours.

This lengthy electrophoresis time period causes drops in the current flow that can exceed 50% at constant voltage. This current drop is caused by the deposition of oppositely charged ions at the anode and cathode of the electrophoresis chamber. During electrophoresis, protons ($H^+$) are formed at the anode and hydroxide ions ($HO^-$) at the cathode as a result of the electrolysis of water. This effect can be quantified by measuring the pH of the liquid buffer solutions in the buffer reservoirs at the anodic and cathodic ends of the electrophoresis chamber. Commonly used buffer solutions have a pH of 8, but following a 16 hour electrophoresis run, the pH can be approximately 10 at the anode and 6 at the cathode. This pH grandient causes slowing of the run and, depending on the relative amounts of sample loaded in a particular lane, can lead to local ion effects that selectively retard migration in the region of a particular sample.

Another factor that can affect the migration patterns is uneven dissipation of the heat that is generated during the course of the electrophoresis run. This heat is a product of the resistance associated with the current passing through the electrophoresis matrix. The above adverse effects can be overcome by circulating the liquid buffer solution between the two buffer reservoirs and over the electrophoresis matrix.

Currently, solution circulation is accomplished by the use of external peristaltic or other non-conducting pumps that are connected by plastic tubing to the two buffer reservoirs. These pumps experience wear and tear and are prone to break down. Also, mechanical pumps require a separate energy supply, are cumbersome to install, and may contaminate the buffer solution. U.S. Pat. 4,702,814 describes non-mechanical circulation of electrophoresis buffer solution by movement of gas bubbles from one electrophoresis buffer receptacle to the other along an inclined conduit. This gas bubble migration concomittantly carries and propels buffer fluid from one receptacle to the other as an inherent part of the bubble migration process.

SUMMARY OF THE INVENTION

The present invention provides an apparatus that circulates buffer solution between an anode-containing reservoir and a cathode-containing reservoir in an electrophoresis device by creating a pressure differential from trapped electrode-produced gases. The circulation apparatus includes a partitioned chamber containing an electrode of the electrophoresis device and communicating with a first reservoir of the electrophoresis device. A horizontal conduit connected to the partitioned chamber is disposed across the electrophoresis matrix bed and opens into the second reservoir of the electrophoresis device.

A fluid pressure differential between the partitioned chamber and the communicating buffer reservoir is created and is the driving force for the flow of the essentially gasless liquid buffer solution through a horizontal channel. The present invention is thus not dependent on a relatively high gas volume and gas velocity for fluid flow, as is the above prior art reference, because gas movement from one reservoir to the other is not required.

Electrode generated gases are trapped within the partitioned chamber and conduit. The trapped gases increase the pressure head and hence lower the buffer solution level in the partitioned chamber and conduit relative to the buffer solution level in the remainder of the electrophoretic apparatus, thus producing a fluid pressure differential. The higher fluid pressure in the partitioned chamber and conduit causes buffer solution flow from the first reservoir, through the partitioned chamber and conduit, and into the second reservoir. The now raised buffer solution fluid level in the second reservoir induces return buffer solution flow.

In a preferred embodiment of the present invention, gas retaining elements in the partitioned chamber augment buffer solution circulation by trapping electrode produced gases under the surface of the buffer solution. An amount of buffer solution equivalent to the volume of the trapped gases is displaced from the partitioned chamber and flows through the conduit to the second reservoir.

In another preferred embodiment, one partitioned chamber enclosing the anode is employed. Two conduits, both communicating with the single partitioned chamber and terminating at the cathode containing reservoir, are employed.

In an alternate embodiment, two partitioned chambers, one in each reservoir, are disclosed. Two conduits, one communicating with each partitioned chamber, carry buffer solution in opposite directions.

BRIEF DESCRIPTION OF THE DRAWINGS

These and other features of the present invention will be more fully appreciated when considered in the light of the following specification and drawings in which:

FIG. 2A is a detail view of a portion of FIG. 2.

DETAILED DESCRIPTION OF THE PREFERRED EMBODIMENT

The present invention is an apparatus providing nonmechanical circulation of buffer solution in an electrophoresis device.

Figure 1:
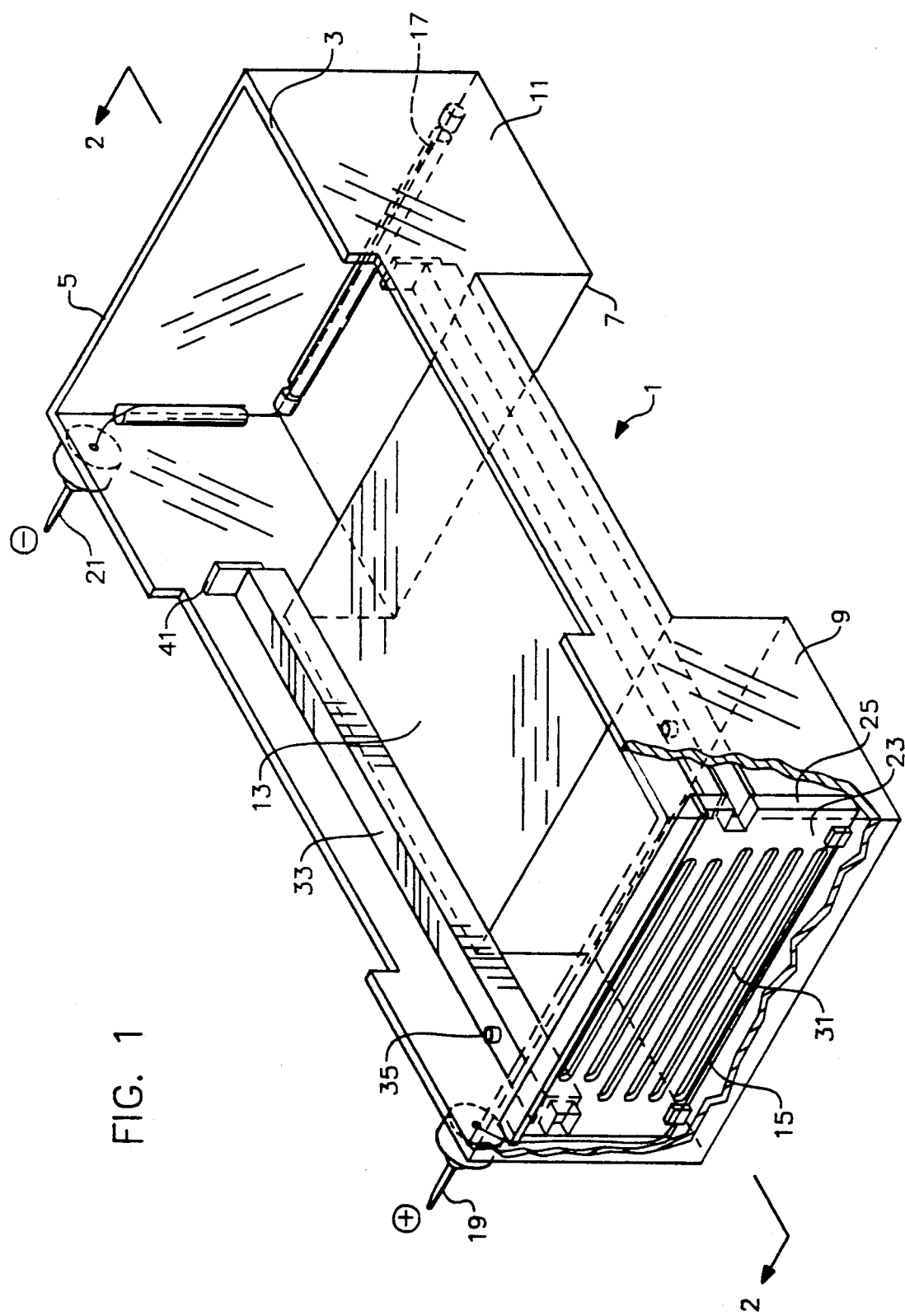
FIG. 1 is an isometric view of a preferred embodiment of the present invention.
Figure 2:
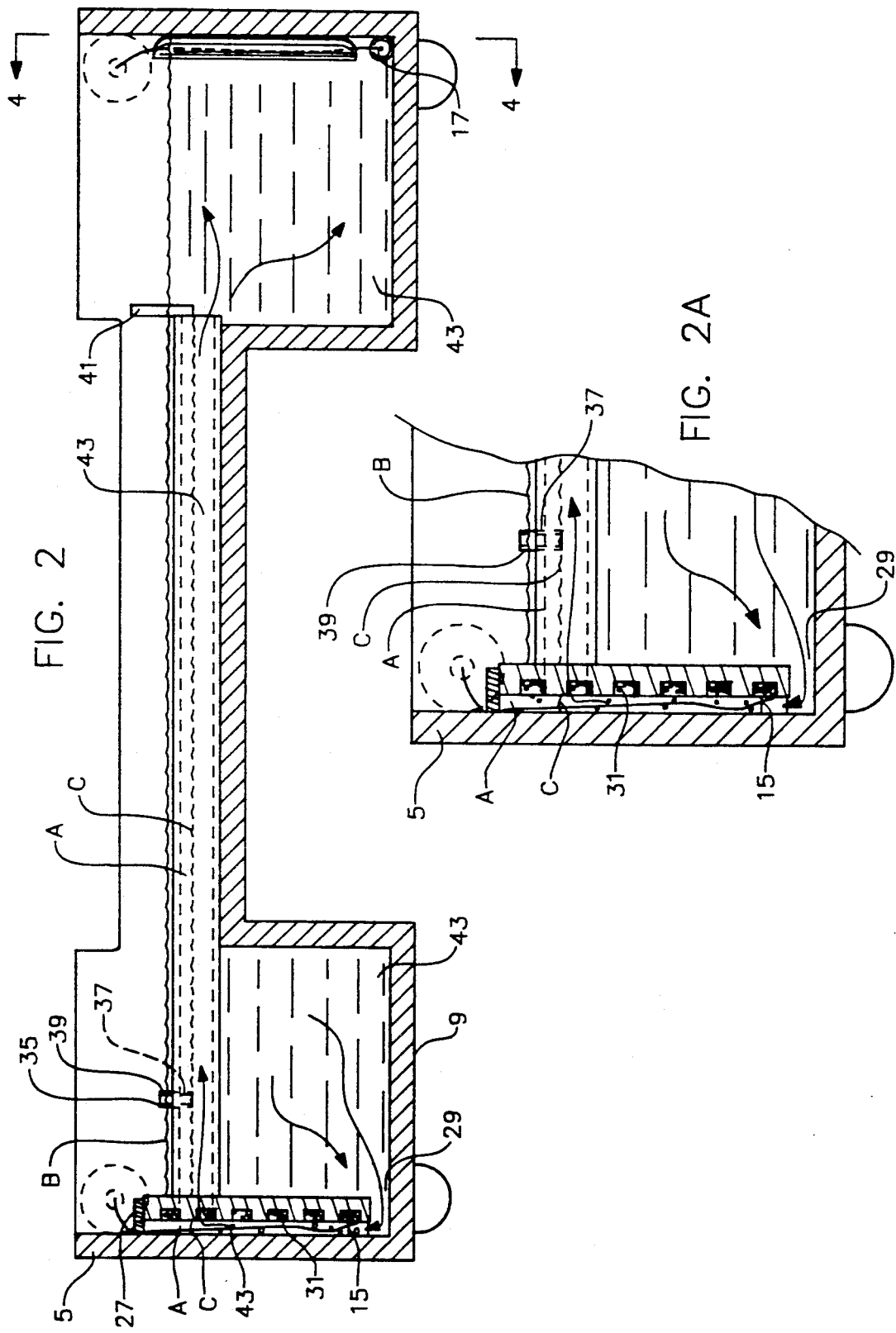
FIG. 2 is a cross-sectional view of the preferred embodiment taken along line 2—2 of FIG. 1.
Figure 3:
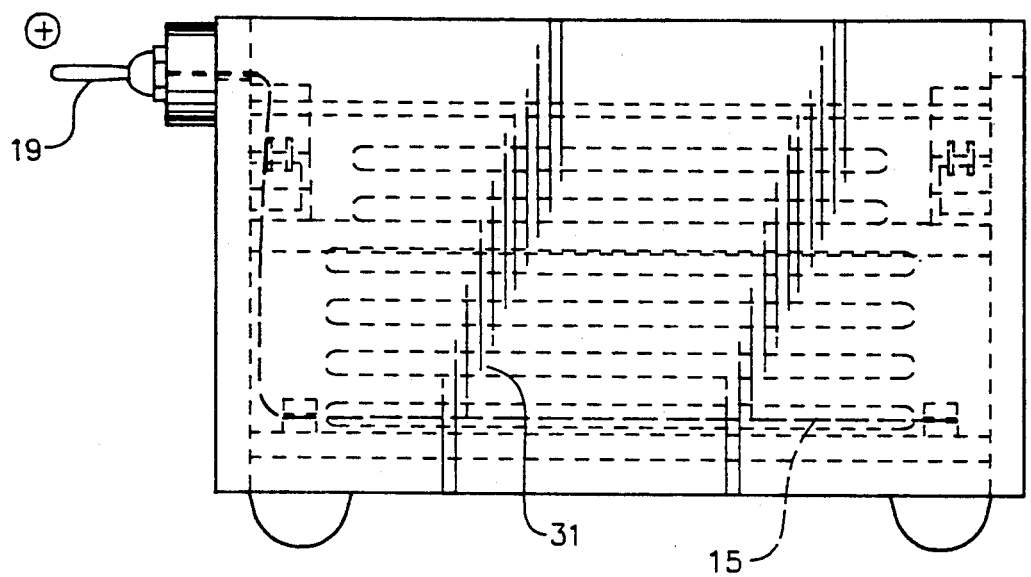
FIG. 3 is an end elevation view of the preferred embodiment of the present invention.
Figure 4:
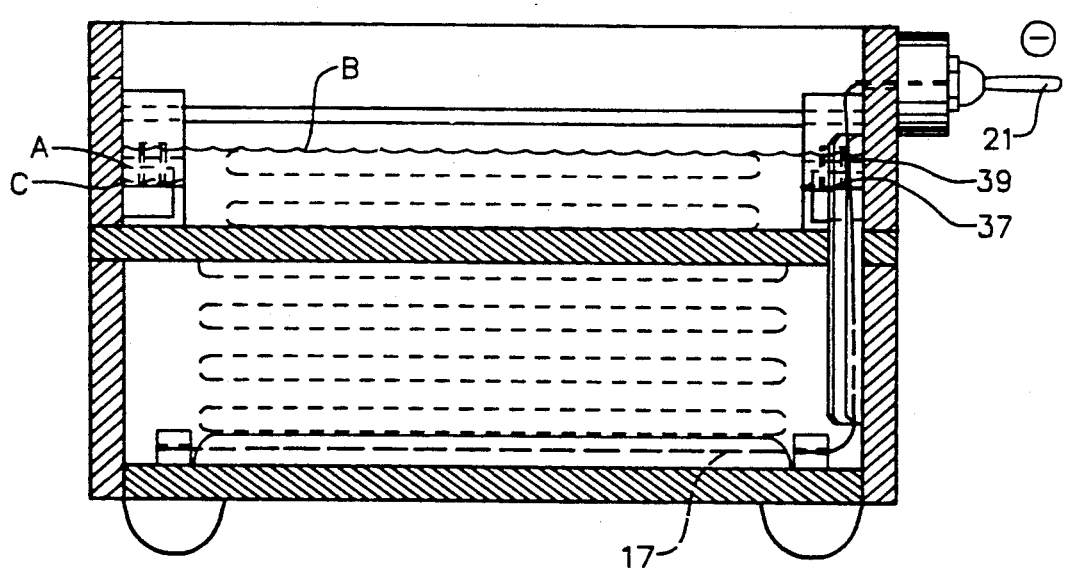
FIG. 4 is a cross-sectional view of the preferred embodiment taken along line 4—4 of FIG. 2.

In FIGS. 1 and 2, electrophoresis device 1 is of generally rectangular box shape including sidewalls 3, end walls 5, base 7 and having at the center a raised matrix bed 13 separating buffer solution reservoirs 9 and 11.

Anode 15 and cathode 17 are located within reservoirs 9 and 11, respectively. Preferably, anode 15 and cathode 17 are located in the bottom of reservoirs 9 and 11 adjacent to end walls 5. Both anode 15 and cathode 17 are preferably comprised of a relatively thin electrically conducting metallic wire. The wires comprising anode 15 and cathode 17 are respectively connected to positive terminal 19 and negative terminal 21 located in side wall 3. Positive terminal 19 and negative terminal 21 are connected to a direct current power supply (not shown).

The circulation apparatus of the present invention, as shown in FIGS. 1–4, includes the following components. Partitioned chamber 23 is preferably comprised of end wall 5, partition 25 and top 27. Partition 25 is preferably substantially parallel t end wall 5 and is affixed in a liquid tight manner, preferably with a chemical adhesive, to side walls 3. Partition 25 is oriented such that fluid flow inlet 29 is present. Fluid from reservoir 9 flows into partitioned chamber 23 through fluid flow inlet 29. Top 27 is preferably adhesively affixed to form an airtight seal to side walls 3, end wall 5, and the upper edge of partition 25.

Conduits 33 are connected to the upper portions of partitioned chamber 23 and extend substantially horizontally across matrix bed 13 to reservoir 11. Two conduits 33 are shown in the preferred embodiment, one on each side of matrix bed 13. However, a single conduit 33 may be employed.

If two partitioned chambers 23 are employed, one enclosing anode 15 and one enclosing cathode 17, one of the two conduits 33 is connected to one partitioned chamber 23 in reservoir 9 and empties into reservoir 11, and the other conduit 33 communicates with the other partitioned chamber 23 in reservoir 11 and empties into reservoir 9. In this manner, fluid is circulated between the two reservoirs 9 and 11 through two conduits 33.

However, in the preferred embodiment, a single partitioned chamber 23 is employed, with conduits 33 connected to only one of reservoirs 9 or 11 so that return fluid flow to partitioned chamber 23 occurs over matrix bed 13 to remove the thermal gradient caused by electrical current flowing through matrix bed 13.

Gas vent tubes 35 are located in the top surface of conduits 33 and are comprised of inner portion 37 and outer portion 39. Barriers 41 are affixed, preferably adhesively, to the upper portion of the ends of conduits 33 adjacent to reservoir 11. The length of barriers 41 covering the ends of conduits 33 is substantially equal to the length of inner portion 37 of vent tubes 35. As discussed below, vent tubes 35 allow optimal venting of anode and cathode gases in conduits 33 in the preferred embodiment. However, vent tubes 35 and barriers 41 are not mandatory for operation of the present invention, and venting of gases will occur out of the ends of conduits 33 as the gas pressure within conduits 33 increases. When barriers 41 are not present, fluid in reservoir 9 does not flow into the ends of conduits 33 even though the buffer solution 43 in reservoir 9 is contacting the electrode produce gases in area A of conduits 33. The pressure of electrode produced gas in area A of conduits 33 and the fluid pressure of the buffer solution 43 in conduits 33 are both greater than the fluid pressure of buffer solution 43 in the top of reservoir 9, thus preventing flow of buffer solution 43 into conduits 33 from reservoir 9.

In operation, the electrophoretic apparatus 1 provides nonmechanical buffer solution flow as follows. Buffer solution 43 preferably fills reservoirs 9 and 11 to buffer solution level B. Buffer solution 43 covers matrix bed 13 and the top surfaces of conduits 33. However, the level B of buffer solution 43 is not to be above outer portion 39 of vent tubes 35.

Initially, prior to electrophoresis, buffer solution 43 also fills partitioned chamber 23 and conduits 33. However, during electrophoresis, gases produced by anode 15 and cathode 17 are trapped in the upper portions of partitioned chamber 23 and conduits 33, thus increasing the pressure head over the buffer solution 43 in partitioned chamber 23 and conduits 33. The buffer solution level C in conduits 33 is preferably a level slightly above the ends of both inner portion 37 of vent tubes 35 and of barriers 41 in conduits 33 during electrophoresis. Thus, during electrophoresis, enclosed area A of trapped anode or cathode produced gases in conduit 33 and chamber 23 cause buffer fluid to recede to level C in conduits 33.

The buffer solution level C in conduits 33 and partitioned chamber 23 cannot rise into the trapped gas area A when the gas pressure in area A is greater than the fluid pressure in conduits 33. The trapped gases in area A increase the pressure head in conduit 33 and partitioned chamber 23 causing a differential fluid pressure between the buffer solution (level C) in conduits 33 and the buffer solution (level B) in matrix bed 13 and reservoirs 9 and 11. The greater fluid pressure within chamber 23 compared to the fluid pressure in matrix bed 13 and reservoirs 9 and 11 causes buffer solution 43 to flow from reservoirs 9 into partitioned chamber 23 through conduits 33 and into reservoir 11 (as shown by the arrows in FIGS. 2 and 2A).

Due to flow of buffer solution 43 into reservoir 11, the buffer solution level B is now greater in reservoir 11 than in reservoir 9, thus inducing buffer solution flow over matrix bed 13 and back into reservoir 11. This circulation continues while the buffer solution level C in conduits 33 is lower than the buffer solution level B in reservoirs 9 and 11 and matrix bed 13.

If sufficient fluid flows out of conduits 33 (or if sufficient anode or cathode produced gas enters area A) to cause the buffer solution level C in conduits 33 to recede below the ends of the inner portion 37 of vent tubes 35 in conduits 33, anode or cathode produced gases will pass out of vent tubes 35. The buffer solution level C will then rise in conduits 33, due to the decrease in gas pressure in area A, until equilibrium is attained. At equilibrium, the buffer solution level C will again be above the ends of the inner portion 37 of vent tubes 35 in conduit 33. Fluid circulation will continue, the buffer solution fluid pressure in conduits 33 being greater than the buffer solution fluid pressure in matrix bed 13 and reservoirs 9 and 11.

Gas retaining elements 31 in partitioned chamber 23 augment the above described buffer solution circulation by trapping anode or cathode produced gas bubbles in partitioned chamber 23 under the surface of buffer solution level C. Thus, an amount of buffer solution 43 equivalent to the volume of the trapped gases is displaced from partitioned chamber 23 and flows through conduits 33 to reservoir 11. This buffer solution flow occurs along conduits 33, and not out of fluid flow inlet 29 and into reservoir 9 because the fluid pressure at the bottom of reservoir 9 is greater than the fluid pressure in partitioned chamber 23 and conduits 33.

While gas retaining elements 31 improve the retention of gas in partitioned chamber 23 under the surface of buffer solution level C, gas will be retained below level C without the presence of gas retaining elements 31. Gas bubbles will adhere to the sides of partitioned chamber 23 as well as end wall 5.

Additionally, gas retaining elements 31, by trapping gases in buffer solution 43 in partitioned chamber 23 minimize the amount of gas venting required by vent tubes 35 because gas build up-in area A is reduced.

It is important to note that fluid flow will occur in the present invention solely based on the above described gas retention below fluid level C in partitioned chamber 23. While the presence of a pressure head in area A as previously described will increase fluid flow, this pressure head is not mandatory.

Testing under controlled conditions demonstrated the nonmechanical circulation of the present invention. A series of duplicate viral DNA samples was electrophoresed in 1% agarose for sixteen hours at a constant voltage of 40 V DC and a current flow of 28 ma in 1.3 liters of electrophoresis buffer (0.04M Tris acetate, 0.002M ethylenediamine tetraacetic acid, pH 8.0). Following the electrophoresis, the pH remained unchanged (8.0) in reservoir 9 and reservoir 11, a 3 ma current drop (10.7%) occurred, and the appearance of the DNA samples in the gel, following ethidium bromide staining, was undistorted.

FIGS. 1 through 4 show a preferred embodiment of the present invention. It will be readily apparent to those skilled in the art that a conventional electrophoresis device employed for zone electrophoresis through a submerged gel matrix is shown. Specific elements, modifying this known device as disclosed in detail above, form the present invention. The use of the illustrated zone electrophoresis device is to be understood as being exemplary of electrophoresis devices in general, and is not intended to limit the invention to the specific device shown. Specifically, the nonmechanical circulation apparatus of the present invention shown may be altered in a manner readily known to those skilled in the art to encompass electrophoresis devices with a matrix of paper, starch or cellulose acetate strip, instead of gel. For the purpose of clarity, however, the description of the preferred embodiment is based on the zone electrophoresis device employing a submerged gel matrix.

While particular embodiments of the present invention have been described in some detail herein above, changes and modifications may be made in the illustrated embodiments without departing from the spirit of the invention.

I claim:

1. A fluid circulation apparatus for an electrophoresis device having at least a first reservoir with a first electrode, at least a second reservoir with a second electrode, and a matrix bed for receiving fluid that has a first fluid level in the first reservoir, second reservoir and matrix bed, said fluid circulation apparatus comprising:
    a partitioned chamber in the first reservoir; and a fluid conduit communicating with said partitioned chamber and extending to the second reservoir whereby said fluid circulation apparatus is disposed to trap electrode produced gas at a level below the first fluid level so that fluid in said fluid circulation apparatus has a pressure head greater than pressure at the first fluid level to cause fluid flow between the first reservoir and the second reservoir through said fluid conduit.

2. The fluid circulation apparatus of claim 1, wherein one of said partitioned chamber and one of said conduit are both located in each of the first reservoir and the second reservoir.

3. The fluid circulation apparatus of claim 1 further comprising:
    secondary electrode gas retaining elements in said partitioned chamber, said secondary gas retaining elements trapping additional electrode produced gas in said partitioned chamber below a second fluid level in said partitioned chamber to circulate an amount of fluid through said fluid circulation apparatus equivalent to the volume of the additional gas trapped in said secondary electrode gas retaining elements.

4. The fluid circulating apparatus of claim 1 further comprising:
    gas venting means in said fluid conduit for venting excess electrode produced gas from said fluid circulation apparatus.

5. An electrophoresis device having fluid circulation comprising:
    a first electrode in a first reservoir;
    a second electrode in a second reservoir;

a matrix bed connecting said first reservoir and said second reservoir for receiving fluid that has a first fluid level in said first reservoir; and a partitioned chamber in said first reservoir; and a fluid conduit communicating with said partitioned chamber and extending to said second reservoir whereby said fluid circulation apparatus is disposed to trap electrode produced gas at a level below the first fluid level so that fluid in said fluid circulation apparatus has a pressure head greater than pressure at the first level to cause flow between said first reservoir and said second reservoir through said fluid conduit.

6. The electrophoresis device of claim 5 further comprising:

secondary electrode gas retaining elements in said partitioned chamber, said secondary electrode gas retaining elements trapping additional electrode produced gas in said partitioned chamber below a second fluid level in said fluid circulation apparatus to circulate an amount of fluid through said fluid circulation apparatus equivalent to the volume of the additional gas trapped in said second electrode gas retaining elements.

7. The electrophoresis device of claim 5 further comprising gas venting means in said fluid conduit for venting excess electrode produced gas from said fluid circulation apparatus.

8. The electrophoresis device of claim 5 further comprising:

a second partitioned chamber in said second reservoir; and a second fluid conduit communicating with said second partitioned chamber and extending to said reservoir.

9. A fluid circulating apparatus for an electrophoresis device having at least a first reservoir with a first electrode, at least a second reservoir with a second electrode, and a matrix bed for receiving fluid that has a first fluid level in the first reservoir, second reservoir and matrix bed, said fluid circulating apparatus comprising:

a partitioned chamber in the first reservoir; and fluid conduit communicating with said partitioned chamber and extending to the second reservoir whereby electrode gas is trapped in said partitioned chamber at a level below the first fluid level so that fluid in said partitioned chamber is displaced to cause fluid flow between the first reservoir and the second reservoir through said fluid conduit.

10. The fluid circulating apparatus of claim 9 further comprising:

gas retaining elements in said partitioned chamber, said gas retaining elements trapping additional electrode produced gas below a second fluid level in said partitioned chamber to circulate an amount of fluid through said fluid conduit equivalent to the volume of the additional gas trapped in said gas retaining element means.

11. The fluid circulating apparatus of claim 10, wherein said gas retaining elements are disposed on the partition of said partitioned chamber.

12. The fluid circulating apparatus of claim 11, wherein said gas retaining elements of a plurality of depressions horizontally disposed on the partition.

13. The fluid circulating apparatus of claim 11, wherein said gas retaining elements are a plurality of protrusions horizontally disposed on the partition of said partitioned chamber.

14. The fluid circulating apparatus of claim 9 further comprising gas venting means in said fluid conduit for venting excess electrode produced gas from said fluid conduit and from said fluid chamber.

* * * * *